US012649060B2

(12) United States Patent
Hu et al.

(10) Patent No.: US 12,649,060 B2
(45) Date of Patent: Jun. 9, 2026

(54) GAIT EVENT-DRIVEN, PHASE-DEPENDENT AND MULTI-MODAL FOOT REHABILITATION SYSTEM AND USE METHOD THEREOF

(71) Applicant: THE HONG KONG POLYTECHNIC UNIVERSITY, Hong Kong (CN)

(72) Inventors: Xiaoling Hu, Hong Kong (CN); Fuqiang Ye, Hong Kong (CN); Waiming Li, Hong Kong (CN); Wei Rong, Hong Kong (CN); Kwok Ting Wong, Hong Kong (CN); Tsz Ching Cheung, Hong Kong (CN); Man-Kit Peter Pang, Hong Kong (CN); Hon-Wah Wai, Hong Kong (CN)

(73) Assignee: The Hong Kong Polytechnic University, Hong Kong (CN)

( * ) Notice: Subject to any disclaimer, the term of this patent is extended or adjusted under 35 U.S.C. 154(b) by 336 days.

(21) Appl. No.: 18/575,356

(22) PCT Filed: Jan. 24, 2022

(86) PCT No.: PCT/CN2022/073495
§ 371 (c)(1),
(2) Date: Jan. 12, 2024

(87) PCT Pub. No.: WO2023/273324
PCT Pub. Date: Jan. 5, 2023

(65) Prior Publication Data
US 2024/0325750 A1 Oct. 3, 2024

(30) Foreign Application Priority Data

Jun. 30, 2021 (CN) .......................... 202110733839.6

(51) Int. Cl.
A61N 1/36 (2006.01)
A61N 1/04 (2006.01)

(52) U.S. Cl.
CPC ....... *A61N 1/36031* (2017.08); *A61N 1/0452* (2013.01); *A61N 1/0476* (2013.01); *A61N 1/0492* (2013.01); *A61N 1/36034* (2017.08)

(58) Field of Classification Search
CPC .. A61N 1/3603; A61N 1/3604; A61N 1/0492; A61N 1/0452; A61N 1/0476
See application file for complete search history.

(56) References Cited

U.S. PATENT DOCUMENTS 4,936,299 A 6/1990 Erlandson
5,070,873 A 12/1991 Graupe et al.
(Continued)

FOREIGN PATENT DOCUMENTS

CN 102579229 B 7/2012
CN 101961527 B 11/2013
(Continued)

OTHER PUBLICATIONS

First Office Action of CN Application No. or patent No. 2021107338396 issued from the China National Intellectual Property Administration on Apr. 30, 2025.
(Continued)

*Primary Examiner* — Alyssa M Alter
(74) *Attorney, Agent, or Firm* — S&F/WEHRW

(57) ABSTRACT

A gait event-driven, phase-dependent and multi-modal foot rehabilitation system, and a use method thereof. The system comprises: a pressure sensor module (110) which measures a pressure distribution value of a foot sole in real time; a micro-control module (111) which compares the measured pressure value with a preset threshold value to identify different gait events in a dynamic gait and a pressure balance (Continued)

Smart device — Wireless transmission — Micro-control module (111)

Neuromuscular electrical stimulation module (100)
Pneumatic musculoskeletal complex module (200)

Vibratory biofeedback module (109) — Stimulation generator (104) — Electric air pump (106) — Electric air valve (107)

Electrode array (103) — Musculoskeletal complex (105)

Fastening integration module (102) — Air pressure sensor (108)

Pressure sensor module (110) — User (101) — Electrode array (103) — Myoelectric signal amplifier (112)

on the inner and outer sides of the foot sole and to control a corresponding operation in real time; a neuromuscular electrical stimulation module (100) which applies or stops a suprathreshold electrical stimulation delivered to a target muscle of the foot on the basis of the recognized gait event; a combined pneumatic musculo-skeletal module (200) which comprises a pneumatic muscle (305) and deflates or inflates the pneumatic muscle (305) on the basis of the recognized gait event; and a vibratory biofeedback module (109) which, when recognizing an imbalance of pressure between the inner side and the outer side of the foot sole, provides a biofeedback to correct the imbalance of force exerted by the foot sole. The gait events comprises heel striking, heel off and sole off. The system can correct foot drop and foot varus, mitigate muscle compensation and dystrophy, and restore a normal gait.

24 Claims, 5 Drawing Sheets

(56) References Cited

U.S. PATENT DOCUMENTS

| | | | |
|---|---|---|---|
| 5,466,213 | A | 11/1995 | Hogan et al. |
| 5,755,645 | A | 5/1998 | Miller et al. |
| 5,830,160 | A | 11/1998 | Reinkensmeyer |
| 6,058,938 | A | 5/2000 | Chu et al. |
| 6,321,116 | B1 | 11/2001 | Mo et al. |
| 6,379,393 | B1 | 4/2002 | Mavroidis et al. |
| 6,500,094 | B1 | 12/2002 | Lin |
| 6,613,000 | B1 | 9/2003 | Reinkensmeyer et al. |
| 6,878,122 | B2 | 4/2005 | Cordo |
| 6,966,882 | B2 | 11/2005 | Horst |
| 10,052,062 | B2 | 8/2018 | De Sapio et al. |
| 2003/0093021 | A1 | 5/2003 | Goffer |
| 2005/0101448 | A1 | 5/2005 | He et al. |
| 2007/0203435 | A1 | 8/2007 | Novak |
| 2007/0282228 | A1 | 12/2007 | Einav et al. |
| 2016/0339240 | A1* | 11/2016 | Mihara ............... A61B 5/6829 |
| 2017/0042467 | A1 | 2/2017 | Herr et al. |
| 2017/0202724 | A1 | 7/2017 | De Rossi et al. |

FOREIGN PATENT DOCUMENTS

| | | |
|---|---|---|
| CN | 103212188 B | 8/2015 |
| CN | 107854774 A | 3/2018 |
| CN | 108113788 A | 6/2018 |
| CN | 108392302 A | 8/2018 |
| CN | 108421162 A | 8/2018 |
| CN | 108938337 A | 12/2018 |
| CN | 108992778 A | 12/2018 |
| CN | 109147904 A | 1/2019 |
| CN | 111345971 A | 6/2020 |
| CN | 111714842 A | 9/2020 |
| CN | 112083807 A | 12/2020 |
| CN | 112315734 A | 2/2021 |
| CN | 112618281 A | 4/2021 |
| CN | 112807194 A | 5/2021 |
| CN | 112826708 A | 5/2021 |
| CN | 213250102 U | 5/2021 |
| JP | 2012176170 A | 9/2012 |
| KR | 20200059829 A | 5/2020 |
| KR | 102239910 B1 | 4/2021 |

OTHER PUBLICATIONS

Extended European Search Report; PCT Application No. PCT/CN2022073495 Issued from the European Patent Office on Jun. 3, 2025.

\* cited by examiner

GAIT EVENT-DRIVEN, PHASE-DEPENDENT AND MULTI-MODAL FOOT REHABILITATION SYSTEM AND USE METHOD THEREOF

FIELD OF THE DISCLOSURE

The present invention relates to the field of auxiliary medical rehabilitation training devices, and in particular to a gait event-driven rehabilitation system that provides a foot dynamic assistance by neuromuscular electrical stimulation, pneumatic musculoskeletal complex and sensory biofeedback in different combinations (i.e., multi-modes) in different gait phases to correct foot drop, strephenopodia and muscle compensation problems for users with lower limb motor function impairments (such as stroke, and spinal cord injury).

BACKGROUND OF THE DISCLOSURE

For users with lower limb motor function impairment, especially users with hemiplegia caused by stroke, their walking gaits exhibit many disabilities, such as bilateral imbalance, foot drop (unable to lift the forefoot), and strephenopodia (the foot turns inward), which greatly increases the user's risk of falling down and inhibits the possibility of later recovery. Meanwhile, long-term gait imbalance leads to dissimilated muscle compensatory movements, making it difficult for the muscles of the affected lower limb to receive effective coordinated rehabilitation training.

In the conventional assistive medical devices, such as ankle-foot orthoses shown in FIG. 1, passive orthoses with fixed joint angles are adopted to provide constant mechanical support and immobilization to avoid foot drop and strephenopodia. However, such orthoses are unable to assist the users in exercising the target muscles of the affected ankle joint, and overuse thereof may cause muscle atrophy and affect the stability of the ankle joint.

In addition, existing robots for lower limb rehabilitation provide a single mechanical external force assistance during the gait process, leading the affected limb to complete a designated gait (such as a specific trajectory). During this process, even if the joint motion generated by the user's own muscle force is inconsistent with the set gait of therobot, it will be forcibly led by the robot's motor, resulting in involuntary passive motion. The auxiliary method of this type of robot cannot guide the user on how to enable the target muscles to correctly exert force and complete the corresponding actions during the exercise process, nor can it give timely feedback signals during the exercise process to allow the user to realize the error and correct it. As a result, the muscle compensatory issues of the user in dynamic gait cannot be corrected and normal gait cannot be effectively restored (i.e., the user cannot restore normal walking without system assistance).

In the existing mechanical and control designs of robots for lower limb rehabilitation, a wearable rehabilitation system that simultaneously corrects foot drop and strephenopodia problems caused by muscle atrophy and muscle compensatory movements or provides error correction feedback during dynamic walking is unknown. In conventional hard exoskeleton robots for lower limb rehabilitation, the design of the ankle joint is too simple in that they all provide a single mechanical moment support and drive in different gait phases and dorsiflexion of the foot in the sagittal plane (ankle joint flexion, the action of the toe moving up toward the shin) and plantar flexion (ankle joint extension, the action of the toe straightening and pressing down to move away from the shin) are generally realized by the rotation of a motor with one degree of freedom. Although this type of design can use the external force from the motor to offset the phenomenon of foot drop, it cannot correct the user's intrinsic muscle atrophy and compensatory movements, and ignores the control and correction of strephenopodia that occurs at the horizontal plane of the foot, which is common after stroke. This mechanical assistance solution may even cause corresponding muscle atrophy due to the lack of freedom in the horizontal plane of the foot. Moreover, the weight of the hard exoskeleton itself makes it prone to loss of balance for unilateral users when walking, especially for hemiplegic users after stroke. A musculoskeletal complex that combines pneumatic muscles (which work by filling an airbag with pressurized air) and an exoskeleton (a hard outer skeletal structure that protects a creature's soft internal organs) is lighter and softer than conventional hard exoskeletons, suitable for unilateral wear on the affected lower limb, and can provide sufficient mechanical assistance.

Neuromuscular electrical stimulation induces calf muscle contraction through transcutaneous stimulation to correct foot drop during the stride phase of gait; at the same time, multi-channel neuromuscular electrical stimulation can correct the compensation of muscle groups. However, single neuromuscular electrical stimulation technology cannot currently be used to correct strephenopodia during the stance phase of gait. The force balance of the plantar horizontal plane at the beginning of the stance phase of gait or the stride phase of gait is sensed by sensors, thus offering the user with instant sensory feedback, such as vibration, sound, light or temperature prompts, etc. The user can independently correct the plantar force distribution to achieve the desired balance range to correct strephenopodia. However, a single plantar sensory balance feedback cannot simultaneously address the problems of foot drop and muscle compensation in complete gait. Through unique multi-modal mechanical and electronic designs, coupled with an innovative phase-dependent, gait event-driven control algorithm, the invention integrates multi-channel neuromuscular electrical stimulation, pneumatic musculoskeletal complex and plantar sensory biofeedbacks and enables them to coordinate with each other in each gait phase. The achieved rehabilitation system can be used to correct foot drop and strephenopodia problems at the same time, and can provide feedback signals in real time to realize the user's independent correction. The coordination ability of lower limb muscle groups and muscle compensation and atrophy are further improved.

SUMMARY OF THE DISCLOSURE

As mentioned above, the existing foot ankle rehabilitation system cannot correct foot drop and strephenopodia in real time during walking and simultaneously improve muscle compensation and muscle atrophy. Specifically, various existing foot ankle rehabilitation systems suffer from the following problems:

1) The conventional ankle and foot orthoses: the entire ankle joint is passively fixed to avoid foot droop and strephenopodia, which, however, will cause muscle atrophy, joint degeneration, and incapability of restoring normal gait.

2) Lower limb rehabilitation robot: the design of the foot ankle is too simple in that they all provide a single mechanical moment support and drive in different gait phases; generally, dorsiflexion and plantarflexion of the foot in the sagittal plane are achieved by rotating a motor with one degree of freedom; and foot drop and strephenopodia cannot be corrected at the same time.

3) Neuromuscular electrical stimulator: currently, a single neuromuscular electrical stimulation technology cannot be used to correct the strephenopodia problem during the stance phase of gait.

In view of the above problems, there is provided a gait event-driven, phase-dependent and multi-modal foot control and feedback rehabilitation system in accordance with the present invention. The system of the present invention is light in weight and is conducive to unilateral use (such as for hemiplegic users) without affecting bilateral balance. Compared to the conventional lower limb rehabilitation robots, the system of the present invention is cheaper and achieves better rehabilitation effects.

In a first example of the present invention, there is provided a gait event-driven, phase-dependent and multi-modal foot rehabilitation system, including:

a pressure sensor module connectable to a foot sole of a user and configured to measure pressure distribution values in different areas of the foot sole in real time;

a micro-control module configured to receive measured pressure values, compare the measured pressure values with a preset threshold value to identify different gait events in dynamic gait and pressure balance in inner and outer sides of the foot sole, and control a neuromuscular electrical stimulation module, a pneumatic musculoskeletal complex module, and/or a vibratory biofeedback module in real time to perform corresponding operations;

the neuromuscular electrical stimulation module configured to perform or stop suprathreshold electrical stimulation of target muscles of the foot based on the gait event identified by the micro-control module;

the pneumatic musculoskeletal complex module including a musculoskeletal complex for providing mechanical support to the foot and configured to deflate or inflate the pneumatic muscles of the musculoskeletal complex based on a gait event identified by the micro-control module to fix the foot ankle during a stance phase of a gait cycle or to relax the foot and the ankle during a stride phase of the gait cycle; and the vibratory biofeedback module configured to provide a biofeedback to correct a force balance of the foot sole of the user when an imbalance of pressure in the inner and outer sides of the foot sole is identified by the micro-control module, wherein the gait event includes heel striking, heel off and sole off.

The pressure sensor module may include a first pressure sensor placed at a first metatarsal head of the foot sole, a second pressure sensor placed at a fifth metatarsal head of the foot sole, and a third pressure sensor placed at a heel.

The micro-control module can identify the gait event in the following manner to achieve real-time control:

$$\begin{cases} E = \text{heel striking ground,} & FSR_{heel}(t) > T_{heel} \\ E = \text{heel off ground,} & FSR_{heel}(t) \le T_{heel} \\ E = \text{sole off ground,} & FSR_1(t) \le T_1 \text{ and } FSR_5(t) \le T_5 \text{ and } FSR_{heel}(t) \le T_{heel} \end{cases}$$

where E is the gait event identified in real time, $FSR_1(t)$, $FSR_5(t)$, and $FSR_{heel}(t)$ are real-time pressure data measured by the first pressure sensor, the second pressure sensor, and the third pressure sensor respectively, and $T_1$, $T_5$, and $T_{heel}$ are the preset threshold values of the first pressure sensor, the second pressure sensor, and the third pressure sensor respectively.

When the pressure value measured by the third pressure sensor is less than the preset threshold value, the micro-control module may identify the gait event as the heel off, controls a pneumatic muscle to deflate and stop mechanical support, and at the same time controls the neuromuscular electrical stimulation module to perform the suprathreshold electrical stimulation on the target muscle.

When the pressure values measured by the first pressure sensor, the second pressure sensor and the third pressure sensor are all less than or equal to their respective preset threshold values, the micro-control module may identify the gait event as the sole off, controls the pneumatic muscle to inflate, and simultaneously controls the neuromuscular electrical stimulation module to perform the suprathreshold electrical stimulation on the target muscle.

The vibratory biofeedback module may provide biofeedback to correct the force balance of the foot sole of the user while performing the suprathreshold electrical stimulation.

When the pressure value measured by the third pressure sensor is greater than the preset threshold value, the micro-control module may identify the gait event as the heel striking, controls the neuromuscular electrical stimulation module to stop the suprathreshold electrical stimulation of the target muscle, and controls the vibratory biofeedback module to stop biofeedback.

The neuromuscular electrical stimulation module may include a stimulation generator and an electrode array, and the electrode array is connected to the stimulation generator via wires to perform the suprathreshold electrical stimulation of the target muscle.

The electrode array may be a dual-channel stimulation electrode array connected to the target muscle, wherein the target muscle is tibialis anterior muscle and gastrocnemius muscle.

The rehabilitation system may further include a myoelectric signal amplifier that may be configured to feedback an electromyographic signal acquired by the electrode array to the micro-control module for calculating muscle dynamic coordination.

The suprathreshold electrical stimulation of the neuromuscular electrical stimulation module may be performed as follows:

$$ES_1 = \begin{cases} 1 & E = \text{sole off ground} \\ 0 & E = \text{heel striking ground} \end{cases}$$

$$ES_2 = \begin{cases} 1 & E = \text{heel off ground} \\ 0 & \text{timing } n \text{ seconds} \end{cases}$$

where $ES_1$ and $ES_2$ are the suprathreshold electrical stimulation performed on the tibialis anterior muscle and the gastrocnemius muscle respectively, E is the gait event identified in real time, 1 means performing the suprathreshold electrical stimulation, and 0 means stopping suprathreshold electrical stimulation.

The suprathreshold electrical stimulation may be a symmetrical square wave electrical stimulation with an amplitude of 70V, a frequency of 40 Hz, and a bandwidth of 50 us.

The pneumatic musculoskeletal complex module may further include an electric air pump, an electric air valve and an air pressure sensor.

The pneumatic musculoskeletal complex module may be further configured to determine the inflation or deflation of the pneumatic muscle in response to comparison of a value of air pressure in the pneumatic muscle measured by the air pressure sensor with a preset pressure threshold.

The musculoskeletal complex may further include an exoskeleton, and the exoskeleton can be used as a container for all electronic devices, control circuit boards and batteries.

The exoskeleton may be 3D printed from polylactide material.

The exoskeleton may be connected to pneumatic muscles via exoskeleton extensions.

The vibratory biofeedback module may include a vibration motor located between a first toe and a second toe of the foot sole.

The vibration motor may be controlled as follows:

$$Z = \begin{cases} 1, & FSR_{1\,max} \le FSR_{5max} \times b\ \% \\ 0, & FSR_{1\,max} > FSR_{5max} \times b\ \%, \text{ or } E = \text{heel striking ground} \end{cases}$$

where Z represents control of the vibration motor, Z=1 represents turning on the vibration motor, Z=0 represents stopping the vibration motor, $FSR_{1max}$ and $FSR_{5max}$ are respectively maximum values of the first pressure sensor at the first metatarsal head and the second pressure sensor at the fifth metatarsal head during a timing period after the heel is off the ground, b % is a preset balance threshold, and E is the gait event identified in real time.

The rehabilitation system may further include a fastening integration module for securing the rehabilitation system to the foot.

The fastening integration module may include a connector for connecting and fixing the exoskeleton and a position fixture for fixing and cushioning a position of the pneumatic muscle.

The fastening integration module may be made of breathable and elastic textile materials.

The pneumatic muscles are polyvinyl chloride films.

In another example of the present invention, there is provided a use method of the aforementioned gait event-driven, phase-dependent and multi-modal foot rehabilitation system is provided.

The scope of the invention is defined by the claims, which are incorporated into this section by reference. Those skilled in the art will gain a more complete understanding of the embodiments of the invention and realize additional advantages thereof from consideration of the following detailed description of one or more embodiments.

BRIEF DESCRIPTION OF THE DRAWINGS

Preferred features, embodiments and variants of the present invention can be seen from the following detailed description, which provides sufficient information for a person skilled in the art to carry out the invention. The detailed description should not be construed as limiting in

Figure 1:
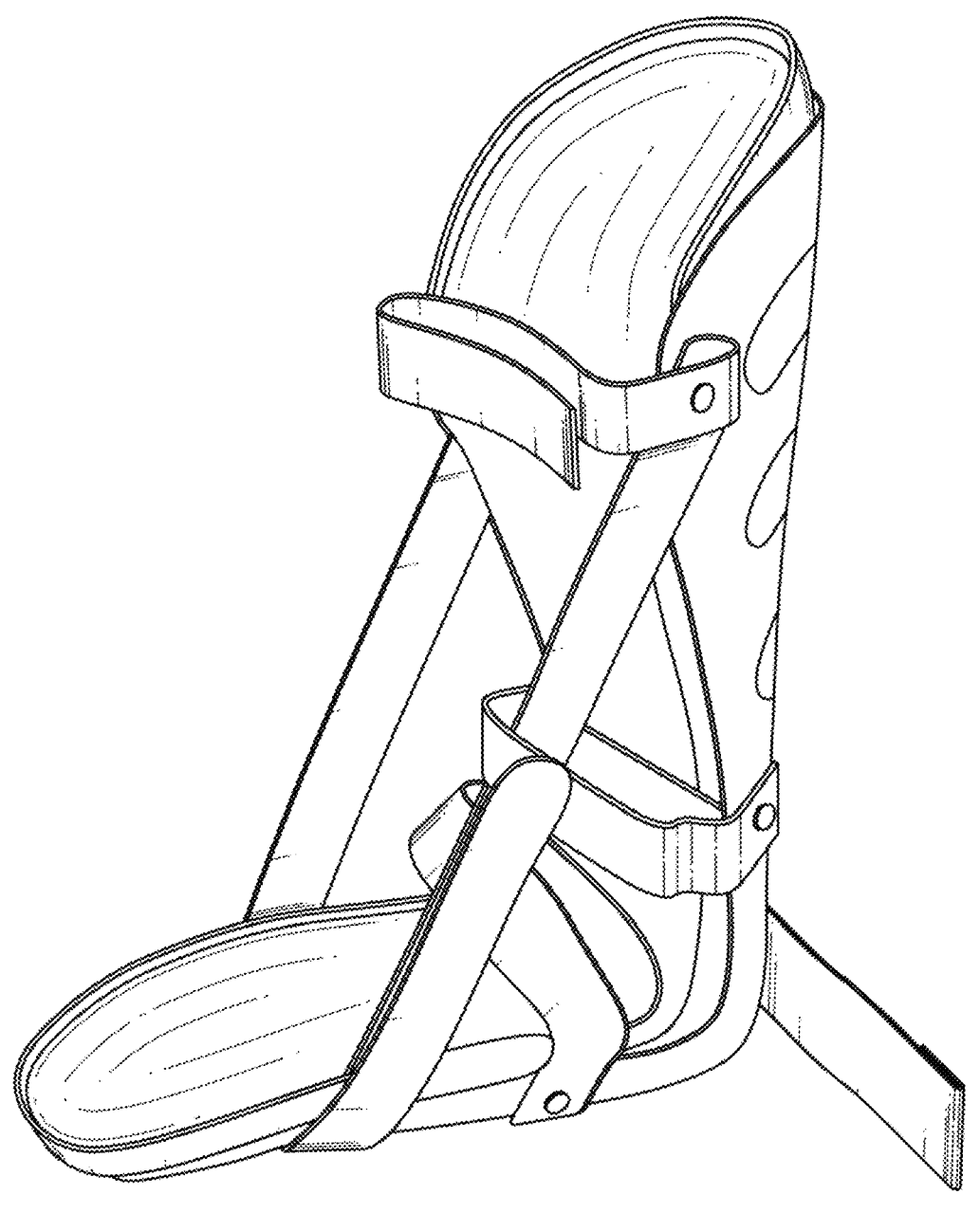

6 any way the scope of the foregoing disclosure. Detailed description will be made with reference to the following multiple drawings:

FIG. 1 shows a picture of a conventional ankle-foot orthosis in the prior art.

Figure 2:
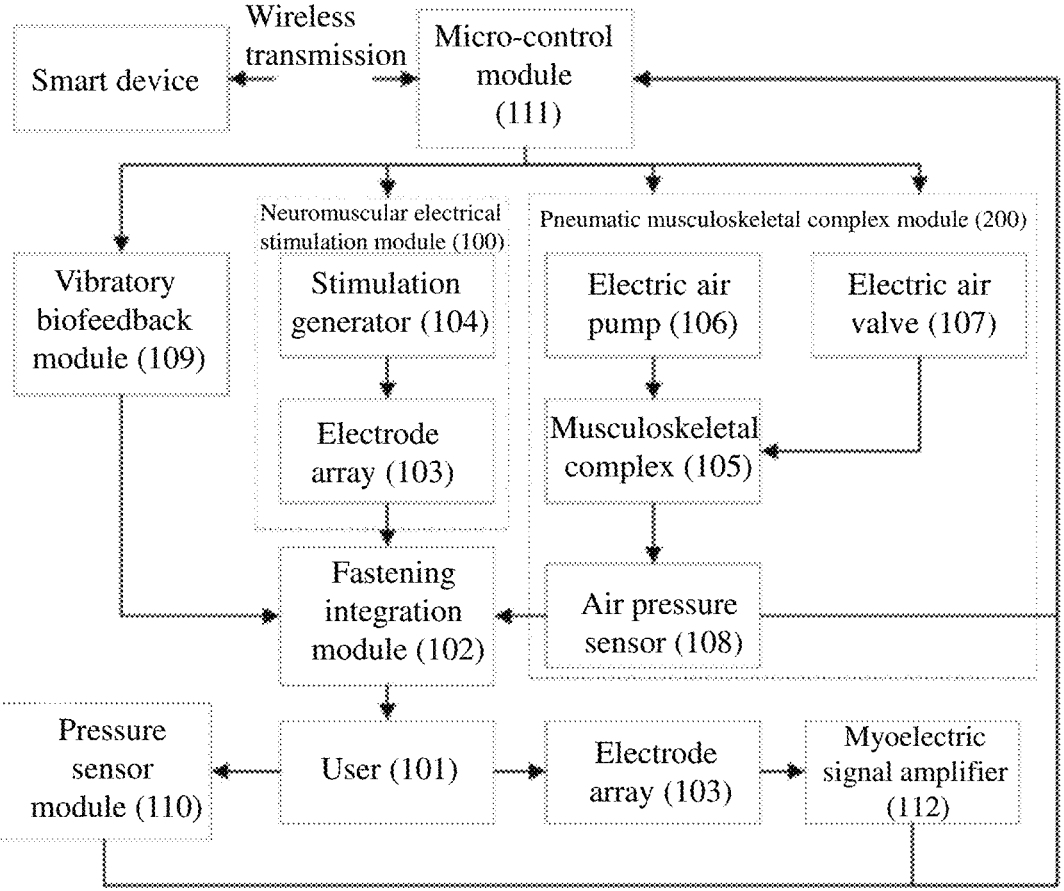

FIG. 2 shows a structural block diagram of a control component of a rehabilitation system according to the present invention.

Figure 3:
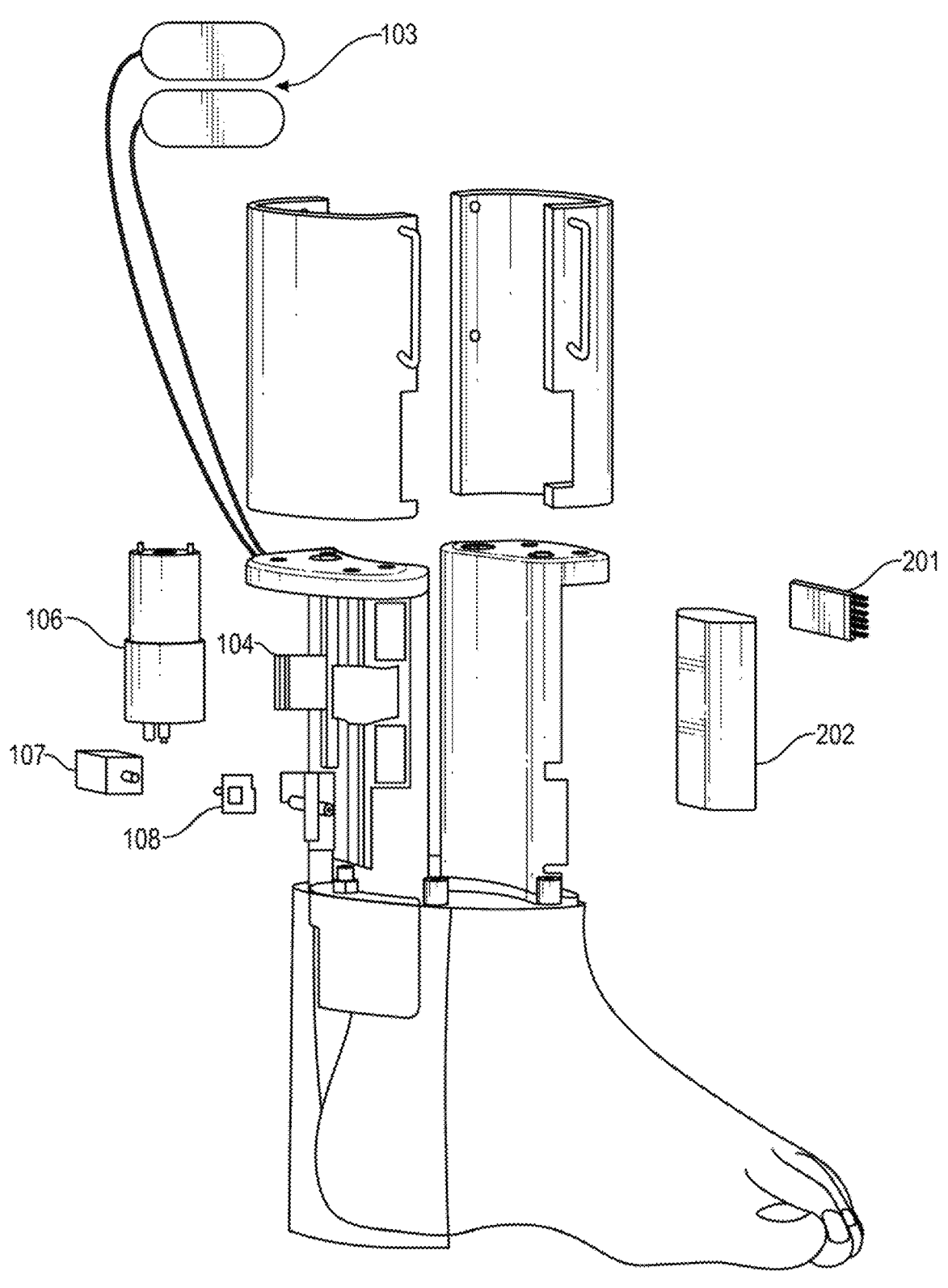

FIG. 3 shows a schematic diagram of a mechanical assembly structure of a pneumatic musculoskeletal complex module and a neuromuscular electrical stimulation module according to embodiments of the present invention.

Figure 4:
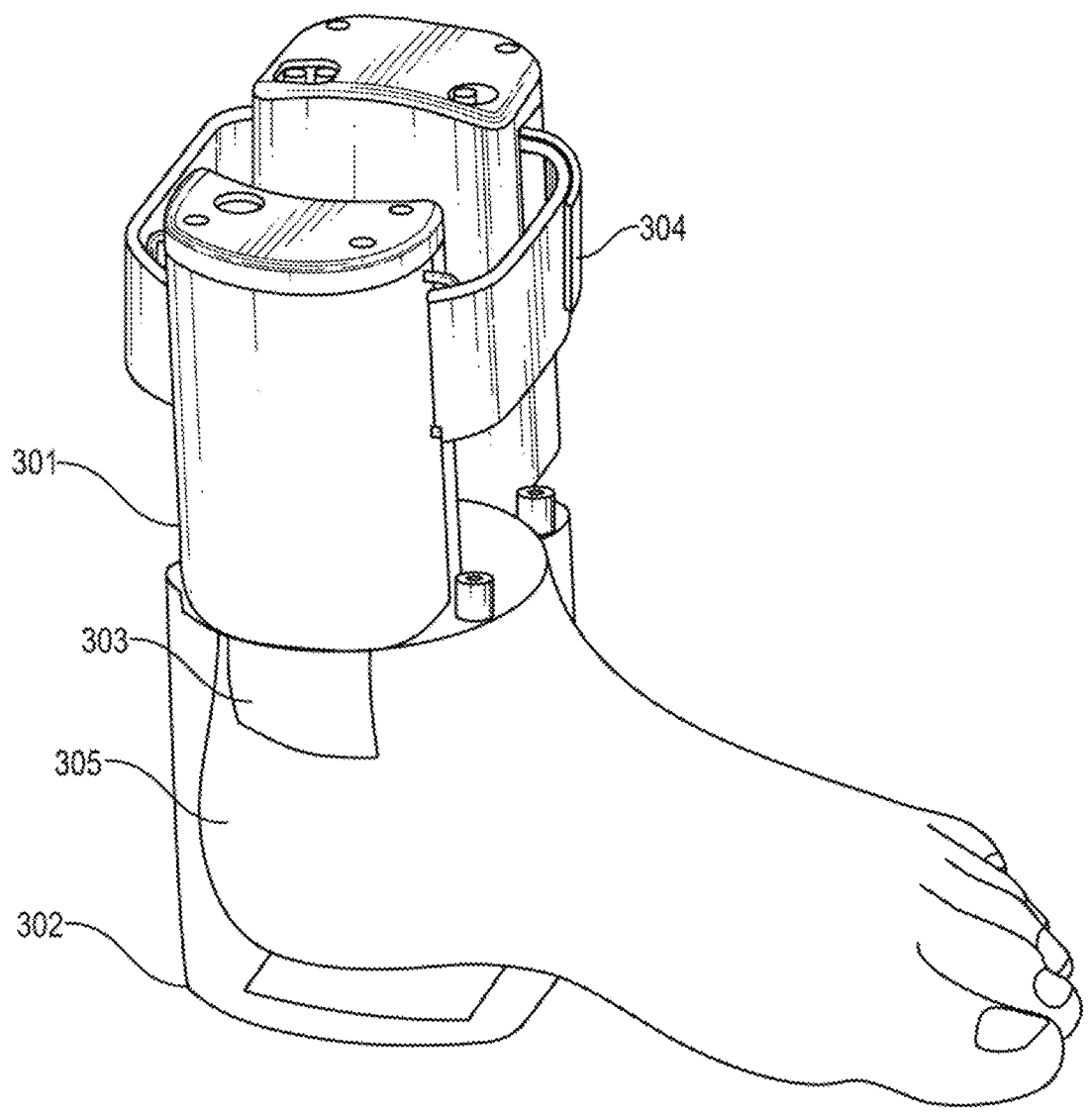

FIG. 4 shows a schematic structural diagram of a pneumatic musculoskeletal complex module wrapped in a fastening integration module according to embodiments of the present invention.

Figure 5:
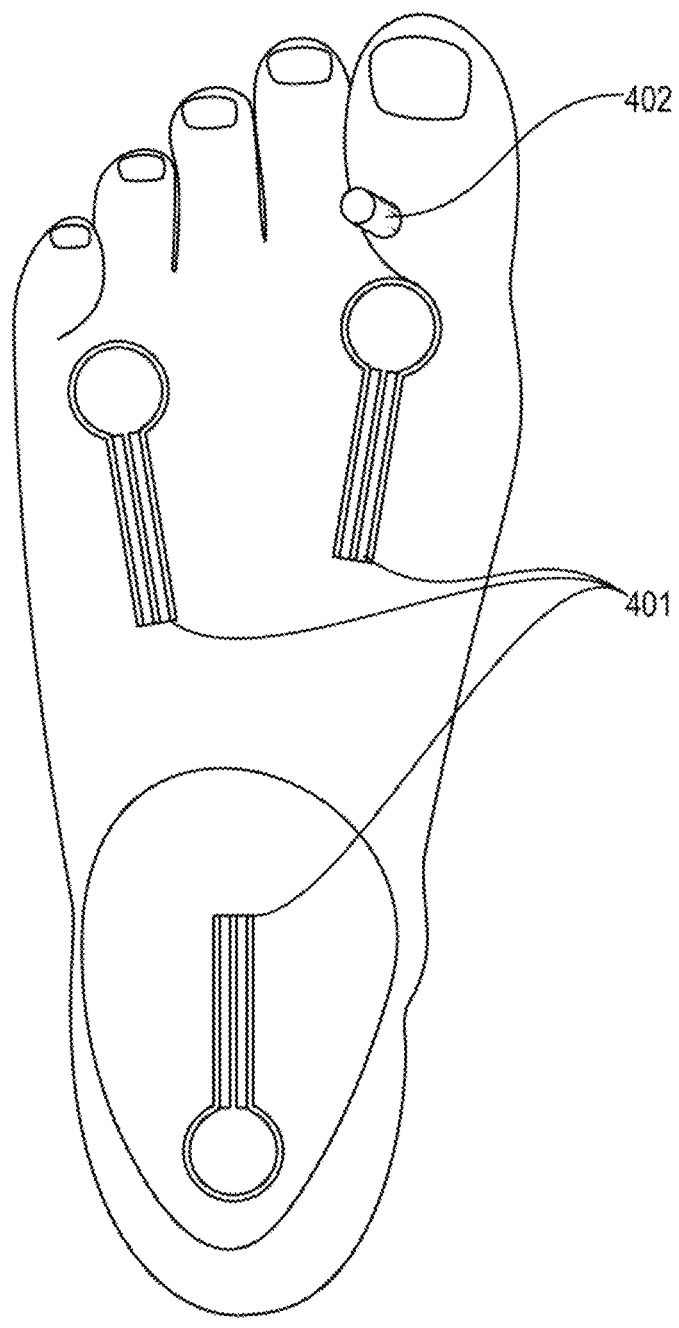

FIG. 5 shows a schematic structural diagram of the distribution of a pressure sensor module and a vibratory biofeedback module at the foot sole according to embodiments of the present invention.

DETAILED DESCRIPTION OF THE EMBODIMENTS

Specific embodiments of the present invention will be described in detail below. The embodiments described herein are illustrative for unilateral use of lower limbs and are not intended to limit the present invention. The system and method proposed by the present invention can also be applicable for bilateral use of the lower limbs.

The present invention provides a gait event-driven, phase-dependent and multi-modal foot control and feedback rehabilitation system and use method thereof, which simultaneously apply multi-channel neuromuscular electrical stimulation, pneumatic musculoskeletal complex and sensory biofeedback for lower limb gait training to enable correction of foot drop and strephenopodia at the same time.

FIG. 2 shows a structural block diagram of the rehabilitation system of the present invention. As shown in FIG. 2, the rehabilitation system of the present invention includes, but not limited to, 1) a pressure sensor module 110; 2) a neuromuscular electrical stimulation module 100; 3) a pneumatic musculoskeletal complex module 200; 4) a vibratory biofeedback module 109; 5) a micro-control module 111; 6) a fastening integration module 102; and 7) a myoelectric signal amplifier 112. The neuromuscular electrical stimulation module 100 includes a stimulation generator 104 and an electrode array 103. The pneumatic musculoskeletal complex module 200 includes an electric air pump 106, an electric air valve 107, a musculoskeletal complex 105 and an air pressure sensor 108. The vibratory biofeedback module 109 includes a vibration motor 402.

The pressure sensor module 110 is used to measure the pressure value of the foot during different gait events in dynamic gait in real time. The micro-control module 111 receives the pressure value measured by the pressure sensor module 110 and identifies different gait events in dynamic gait and the pressure balance in inner and outer sides of the foot sole to drive the corresponding functional modules to provide neuromuscular electrical stimulation, mechanical assistance and vibration biofeedback, respectively. The functional modules include the neuromuscular electrical stimulation module 100, the pneumatic musculoskeletal complex module 200, and the vibratory biofeedback module 109. For example, the pressure sensor module 110 may include a plurality of pressure sensors. In one embodiment of the present invention, three pressure sensors may be provided, where a first pressure sensor is placed at a first metatarsal head of the foot, a second pressure sensor is placed at a fifth metatarsal head of the foot, and the third pressure sensor is placed at the heel. For example, each pressure sensor can be placed on the corresponding foot sole by adhesive means.

FIGS. 3-5 show schematic structural diagrams of the system for the ankle joint of the present invention, which can simultaneously correct foot drop and strephenopodia problems of the lower limbs and improve muscle compensation. The rehabilitation system of the invention will be further described below with reference to FIGS. 3-5.

Specifically, FIG. 3 shows a schematic diagram of the mechanical assembly structure of the pneumatic musculoskeletal complex module and the neuromuscular electrical stimulation module according to embodiments of the present invention. FIG. 4 shows a schematic structural diagram of the pneumatic musculoskeletal complex wrapped in the fastening integration module according to embodiments of the present invention. FIG. 5 shows a schematic structural diagram of the distribution of the pressure sensor and vibratory biofeedback module at the foot sole according to embodiments of the present invention.

In one embodiment according to the present invention, the electrode array 103 is connected to (for example, with adhesive stimulation electrodes, may be adhered to) the skin surface of the tibialis anterior muscles and gastrocnemius muscles on the affected side of the user's foot (transcutaneous stimulation), and is connected to the stimulation generator 104 by wires, and then electrical stimulation is applied to the target muscles of the foot through the micro-control module 111 to help the user correct foot drop and strephenopodia caused by muscle disorders. In this embodiment, electrical stimulation may be applied to the target muscle, and corresponding muscle electrical signals may also be acquired, and the acquired electromyographic signals are fed back to the micro-control module 111 through the myoelectric signal amplifier 112 for calculating muscle dynamic coordination. As shown in FIG. 3, the electrode array 103 may include two electrodes, for example.

The battery 202 powers the entire rehabilitation system and may be a rechargeable battery or a disposable battery. A wireless transmission chip 201 is configured to implement wireless information interaction between the micro-control module 111 and a smart device.

As shown in FIG. 4, the pneumatic musculoskeletal complex includes artificial muscles 305 and exoskeletons 301 fixed on both sides of the ankle joint. The exoskeleton 301 can be used as a container (i.e., control box) that can accommodate all electronic devices, control circuit boards and batteries. Artificial muscles may be electric field-driven artificial muscles, gas-driven artificial muscles (pneumatic muscles), heat-driven artificial muscles, solvent absorption-driven artificial muscles, electrochemical-driven artificial muscles, etc. In the embodiment of the present invention, for example, the pneumatic muscle 305 is selected as the artificial muscle of the present invention. The pneumatic muscle 305 may be an airbag that can be inflated by pressurized air, and may be made of a film material, such as a polyvinyl chloride film or other materials with less deformation when inflated. The pneumatic muscles 305 are controlled by the micro-control module 111 and are connected to the electric air pump 106, the electric air valve 107 and the air pressure sensor 108 through gas conduit(s), thereby realizing the inflation of the pneumatic muscles and maintaining air pressure and deflation.

The exoskeleton 301 has a curved shape, which may be 3D printed from a polylactide material, for example. Exoskeleton 301 may be connected to the pneumatic muscles 305 via exoskeleton extensions 303. When the micro-control module 111 triggers the pneumatic muscles 305 to inflate and maintain the inflation state under the air pressure, the pneumatic muscles 305 and the exoskeleton 301 work together as a musculoskeletal complex to provide mechanical support for the ankle joint to stabilize the mechanical structure of the ankle joint and prevent strephenopodia. After deflation, the pneumatic muscles 305 become soft, allowing the ankle joint to complete plantar flexion with a high degree of freedom without external assistance to exercise muscle strength at the ankle joint and prevent muscle atrophy.

The fastening integration module 102 for fixing the rehabilitation system to the user's foot may be made of, for example, a breathable elastic textile material to integrate the pneumatic musculoskeletal complex and wires therein. The fastening integration module 102 may include a connector 304 for connecting and fixing the control box composed of the exoskeleton 301 on both sides of the ankle joint, thereby facilitating the wearing of the system and enhancing wearing comfort. In one embodiment of the present invention, the connecting member 304 may be, for example, an elastic Velcro with a certain elasticity. The fastening integration module 102 may also include a position fixture 302, which is used to fix and cushion the position of the pneumatic muscle 305 when the pneumatic muscle 305 is inflated and deflated. In one embodiment of the invention, the position fixture 302 can be made of, for example, a breathable textile material. The breathable textile material has a certain degree of elasticity to facilitate position fixation and cushioning. In addition, the position fixture 302 can wrap the wires between the pressure sensor module 110 and the vibratory biofeedback module 109 at the foot sole and the control box.

Referring to FIG. 5, three (for example, film-like) pressure sensors 401 are connected to the micro-control module 111 through circuit wires, where the first pressure sensor is placed at the first metatarsal head, the second pressure sensor is placed at the fifth metatarsal head, and the third pressure sensor is placed at the heel. The signals from the pressure sensors are used to identify gait events in real time and calculate plantar balance to control the cooperation of each functional module of the system at different phases. The vibration motor 402 is placed between the first toe and the second toe, and is connected to the micro-control module 111 through circuit wires. During the gait process, the vibration motor 402 provides necessary vibration biofeedback, prompting the user to actively adjust the force balance on the foot sole to correct the strephenopodia problem.

In the present invention, when the foot is in the process of dynamic gait, the system identifies gait events in the following method to achieve real-time control:

$$\begin{cases} E = \text{heel striking ground,} & FSR_{heel}(t) > T_{heel} \\ E = \text{heel off ground,} & FSR_{heel}(t) \le T_{heel} \\ E = \text{sole off ground,} & FSR_1(t) \le T_1 \text{ and } FSR_5(t) \le T_5 \text{ and } FSR_{heel}(t) \le T_{heel} \end{cases} \quad (1)$$

where E represents the gait event identified in real time, $FSR_1(t)$, $FSR_5(t)$, and $FSR_{heel}(t)$ are the real-time pressure data of the first pressure sensor at the first metatarsal head, the real-time pressure data of the second pressure sensor at the fifth metatarsal head, and the real-time pressure data of the third pressure sensor at the heel respectively. $T_1$, $T_5$, and $T_{heel}$ are threshold intensities of the first pressure sensor, the second pressure sensor, and the third pressure sensor respectively. The threshold intensity can be set as needed, and is preset to a certain percentage of the maximum value of each pressure sensor during dynamic gait, such as 40%, for example.

In the initialization state, the heel of the affected side steps on the ground, and the pneumatic muscles 305 in the pneumatic musculoskeletal complex module 200 are in an inflated state to provide mechanical support.

I) When the pressure value of the third pressure sensor at the heel is less than or equal to the set threshold value, the system identifies it as a "heel off" event (start of stride phase). The micro-control module 111 triggers the pneumatic muscles 305 in the pneumatic musculoskeletal complex module 200 to enter the deflation state, stops mechanical support, and performs suprathreshold electrical stimulation on the target muscles (such as gastrocnemius) through the neuromuscular electrical stimulation module 100 to achieve ankle plantar flexion. II) After timing a certain fixed time value, such as 2 seconds, the system stops releasing electrical stimulation to the target muscle (such as gastrocnemius) through the micro-control module 111; at the same time, the system uses the plantar pressure of the ankle plantar flexion to determine whether to command vibratory biofeedback module 109 to provide vibration biofeedback so as to correct plantar force balance. III) When the values from all the first, second, and third pressure sensors to be less than or equal to their respective preset thresholds, the system identifies it as a "sole off" event (in the middle of the stride phase), and triggers the pneumatic muscle 305 in the pneumatic musculoskeletal complex module 200 via the micro-control module 111 to inflate and simultaneously releases suprathreshold electrical stimulation to the target muscle (such as tibialis anterior muscle) to achieve ankle dorsiflexion (correcting foot drop). At this time, the vibratory biofeedback module 109 provides necessary vibration biofeedback to remind the user 101 to improve balance at the foot sole in the subsequent stance phase. IV) When the pressure value of the third pressure sensor at the heel is greater than the set threshold value, the system identifies it as a "heel striking" event (start of the stance phase), and controls the micro-control module 111 to cause the neuromuscular electrical stimulation module 100 to stop releasing electrical stimulation to the target muscle. (such as the tibialis anterior muscle), and the vibratory biofeedback module 109 stops the vibration biofeedback. At this time, the air pressure value in the pneumatic muscle 305 reaches the maximum. V) When the pressure value of the third pressure sensor at the heel is less than the threshold value, the system identifies it as "heel off" event (start of the stride phase), and the gait enters the cycle process.

The neuromuscular electrical stimulation module 100 includes an electrode array 103 and a stimulation generator 104. In this embodiment, the electrode array 103 is a dual-channel stimulation electrode array. The dual-channel stimulation electrode array is attached to the antagonistic muscle pairs (such as tibialis anterior and gastrocnemius muscles) of the controlled joint activities (such as ankle dorsiflexion and plantar flexion) to perform alternating, phase-dependent transcutaneous electrical stimulation to induce the effective contraction of target muscles in the relevant phase for guiding the muscle coordination involved in ankle dorsiflexion and plantar flexion during gait. Neuromuscular electrical stimulation is controlled in the following ways:

$$ES_1 = \begin{cases} 1 & E = \text{sole off ground} \\ 0 & E = \text{heel striking ground} \end{cases} \quad (2)$$

$$ES_2 = \begin{cases} 1 & E = \text{heel off ground} \\ 0 & \text{timing } n \text{ seconds} \end{cases} \quad (3)$$

where $ES_1$ and $ES_2$ respectively represent the suprathreshold neuromuscular electrical stimulation on the target muscles (i.e., tibialis anterior and gastrocnemius muscles). The stimulation intensity is preset to a fixed value in advance according to the user's conditions, such as symmetrical square wave electrical stimulation with amplitude of 70V, frequency of 40 Hz, and bandwidth of 50 us. When the sole is off the ground during dynamic gait, the system provides corresponding electrical stimulation ($ES_1$=1) to cause the tibialis anterior muscle to contract, driving the ankle joint to complete dorsiflexion activities. When the heel strikes the ground, the system stops this electrical stimulation ($ES_1$=0). When the heel lifts off the ground, the system provides corresponding electrical stimulation ($ES_2$=1) to cause the gastrocnemius muscle to contract, driving the ankle joint to complete plantar flexion activities. This neuromuscular electrical stimulation time is the preset fixed time, n seconds, such as 2 seconds. After timing 2 seconds, the system stops this electrical stimulation ($ES_2$=0). The stimulation electrode array can also acquire muscle electrical signals from the skin surface through the stimulation electrodes, which is fed back to the micro-control module 111 after amplification via the myoelectric signal amplifier.

The pneumatic musculoskeletal complex module 200 includes, but is not limited to: a musculoskeletal complex 105 that combines pneumatic muscles 305 with an exoskeleton 301, an electric air valve 107, an electric air pump 106 and an air pressure sensor 108, which are controlled in the following manner:

$$\begin{cases} P = 1, V = 0 & E = \text{sole off ground, and } Ap \le Tp \\ P = 0, V = 0 & Ap > Tp \\ P = 0, V = 1 & E = \text{heel off ground} \end{cases} \quad (4)$$

where P and V represent the control of the electric air pump 106 and the electric air valve 107 respectively, Ap and Tp are the air pressure value and the preset pressure threshold in the pneumatic muscle 305 respectively, and the preset pressure threshold is set according to the user's customization. When it is identified that the sole is off the ground and the air pressure in the pneumatic muscles 305 is less than or equal to the preset threshold value, the system turns on the electric air pump 106 and closes the electric air valve 107 to trigger the inflated state of the pneumatic muscles 305 to provide mechanical support at the target joint position. When the air pressure in the pneumatic muscle 305 is greater than the preset threshold value, the system stops the electric air pump 106 from inflating and closes the electric air valve 107 to maintain the air pressure in the pneumatic muscle 305 near the preset threshold to prevent damage to the pneumatic muscle 305 caused by over-inflation. When it is identified that the heel is off the ground, the system stops the electric air pump 106 from inflating and opens the electric air valve 107, triggering the pneumatic muscles 305 to deflate to achieve free movement of the ankle joint during striking. The exoskeleton 301 and its extension 303 in the musculoskeletal complex 105 adopt an arc-shaped design to fit the user's calf, and together with the pneumatic muscles provide mechanical support for the joints to help fix their angles and prevent soft tissue injury caused by strephenopodia.

In one embodiment of the present invention, the vibratory biofeedback module 109 may be a vibration motor 402 located between the first toe and the second toe of the foot, which is, based on the real-time pressure data $FSR_1$ of the first pressure sensor at the first metatarsal head. and real-time pressure data $FSR_5$ from the second pressure sensor at the fifth metatarsal head, is operated and controlled as follows:

$$Z = \begin{cases} 1, & FSR_{1\,max} \leq FSR_{5max} \times b\ \% \\ 0, & FSR_{1\,max} > FSR_{5max} \times b\ \%,\ \text{or}\ E = \text{heel striking ground} \end{cases} \quad (5)$$

where Z represents the control of the vibration motor 402, $FSR_{1max}$ and $FSR_{5max}$ are respectively the maximum values of the first pressure sensor at the first metatarsal head and the second pressure sensor at the fifth metatarsal head during the timing after the heel is off the ground, b % is the preset balance threshold value, such as 50%. If $FSR_{5max}$ multiplied by the preset balance threshold is still greater than or equal to $FSR_{1max}$, the system identifies it as gait imbalance and turns on the vibration motor 402 (Z=1) to provide vibration biofeedback to remind the user 101 to adjust the force balance of the affected foot sole, and the vibration intensity is the mechanical vibration threshold that the user can perceive. If $FSR_{5max}$ multiplied by the preset balance threshold is less than $FSR_{1max}$, the system does not trigger the vibration motor 402 (Z=0), that is, the balance at the foot sole reaches the standard. When a heel striking event is identified, the system turns off the vibration motor 402 and stops the vibration biofeedback.

The micro-control module 111 receives the real-time signals of the sequential pressure sensor module 110 and the air pressure sensor 108 to identify gait events, and issues instructions to control the operations of the neuromuscular electrical stimulation module 100, the pneumatic musculoskeletal complex module 200 and the vibratory biofeedback module 109 in real time. At the same time, the micro-control module 111 receives the muscle electrical signals measured by the stimulation electrode array 103, and after normalization calculation, obtains real-time automated assessment parameters, transmits them to the smart device in a wireless data exchange manner, and upload the training records and assesses parameters to the cloud server for archiving, management and analysis by medical staff. Automated assessment parameters include but are not limited to: muscle activation level and antagonist muscle pair synergistic contraction index, and smart devices include but are not limited to: smart phones, smart tablets, and portable computers.

The system and method of the present invention offer the following advantages:

1) Multi-modal (fusion of multiple assistive technologies), phase-dependent real-time control method is used to simultaneously correct foot drop and strephenopodia, and improve muscle compensation and atrophy to restore normal gait.

2) Structural design of wearable foot ankle multi-modal system.

3) Biofeedback signals are given to allow users to correct balance at the foot sole independently.

4) muscle coordination is improved to prevent muscle atrophy through neuromuscular electrical stimulation.

In addition to being used to simultaneously correct foot drop and inversion problems for users with unilateral hemiplegia as set forth in the embodiments, this lower limb movement rehabilitation system may also be online and paired to facilitate use by users with bilateral paralysis, such as users with spinal cord injuries, to provide them with training of bilateral lower limb movement rehabilitation.

While this disclosure has been described in terms of limited embodiments, those skilled in the art having the benefit of this disclosure will appreciate that other embodiments may be devised without departing from the scope of the disclosure as set forth herein. Accordingly, the scope of the disclosure should be limited only by the appended claims.

The invention claimed is:

1. A gait event-driven, phase-dependent and multi-modal foot rehabilitation system, the system comprising:

a pressure sensor module (110) connectable to a foot sole of a user and configured to measure pressure distribution values in different areas of the foot sole in real time;

a micro-control module (111) configured to receive measured pressure values, compare the measured pressure values with preset threshold values to identify different gait events in dynamic gait and pressure balance in inner and outer sides of the foot sole, and control a neuromuscular electrical stimulation module (100), a pneumatic musculoskeletal complex module (200), and a vibratory biofeedback module (109) in real time to perform corresponding operations;

the neuromuscular electrical stimulation module (100) configured to perform or stop suprathreshold electrical stimulation for target muscles of the foot based on a gait event identified by the micro-control module (111);

the pneumatic musculoskeletal complex module (200) comprising a musculoskeletal complex (105) for providing mechanical support to the foot and configured to deflate or inflate pneumatic muscles (305) of the musculoskeletal complex (105) based on the gait event identified by the micro-control module (111) to fix a foot ankle during a stance phase of a gait cycle or to relax the foot ankle during a stride phase of the gait cycle; and the vibratory biofeedback module (109) configured to provide a biofeedback to correct a force balance of the foot sole of the user when an imbalance of pressure in the inner and outer sides of the foot sole is identified by the micro-control module (111), wherein the gait event comprises heel striking, heel off and sole off.

2. The foot rehabilitation system of claim 1, wherein the pressure sensor module (110) comprises a first pressure sensor placed at a first metatarsal head of the foot sole, a second pressure sensor placed at a fifth metatarsal head of the foot sole, and a third pressure sensor placed at a heel.

3. The foot rehabilitation system of claim 2, wherein the micro-control module (111) identifies the gait event in the following manner to achieve real-time control:

$$\begin{cases} E = \text{heel striking ground,} & FSR_{heel}(t) > T_{heel} \\ E = \text{heel off ground,} & FSR_{heel}(t) \le T_{heel} \\ E = \text{sole off ground,} & FSR_1(t) \le T_1 \text{ and } FSR_5(t) \le T_5 \text{ and } FSR_{heel}(t) \le T_{heel} \end{cases}$$

where E is the gait event identified in real time, $FSR_1(t)$, $FSR_5(t)$, and $FSR_{heel}(t)$ are real-time pressure data measured by the first pressure sensor, the second pressure sensor, and the third pressure sensor respectively, and $T_1$, $T_5$, and $T_{heel}$ are preset threshold values of the first pressure sensor, the second pressure sensor, and the third pressure sensor respectively.

4. The foot rehabilitation system of claim 3, wherein when a pressure value measured by the third pressure sensor is less than a preset threshold value, the micro-control module (111) identifies the gait event as the heel off, controls the pneumatic muscle (305) to deflate and stop mechanical support, and at the same time controls the neuromuscular electrical stimulation module (100) to perform the suprathreshold electrical stimulation on the target muscles.

5. The foot rehabilitation system of claim 3, wherein when pressure values measured by the first pressure sensor, the second pressure sensor and the third pressure sensor are all less than or equal to their respective preset threshold values, the micro-control module (111) identifies the gait event as the sole off, controls the pneumatic muscle (305) to inflate, and at the same time controls the neuromuscular electrical stimulation module (100) to perform the suprathreshold electrical stimulation on the target muscles.

6. The foot rehabilitation system of claim 5, wherein the vibratory biofeedback module (109) provides biofeedback to correct the force balance of the foot sole of the user while performing the suprathreshold electrical stimulation.

7. The foot rehabilitation system of claim 3, wherein when a pressure value measured by the third pressure sensor is greater than a preset threshold value, the micro-control module (111) identifies the gait event as the heel striking, controls the neuromuscular electrical stimulation module (100) to stop the suprathreshold electrical stimulation of the target muscle, and controls the vibratory biofeedback module (109) to stop biofeedback.

8. The foot rehabilitation system of claim 1, wherein the neuromuscular electrical stimulation module (100) comprises a stimulation generator (104) and an electrode array (103), and the electrode array (103) is connected to the stimulation generator (104) via wires to perform the suprathreshold electrical stimulation of the target muscles.

9. The foot rehabilitation system of claim 8, wherein the electrode array (103) is a dual-channel stimulation electrode array connected to the target muscles, and wherein the target muscles are tibialis anterior muscle and gastrocnemius muscle.

10. The foot rehabilitation system of claim 8, wherein the rehabilitation system further comprises a myoelectric signal amplifier (112) that is configured to feedback an electro-myographic signal acquired by the electrode array (103) to the micro-control module (111) for calculating muscle dynamic coordination.

11. The foot rehabilitation system of claim 9, wherein the suprathreshold electrical stimulation of the neuromuscular electrical stimulation module (100) is as follows:

$$ES_1 = \begin{cases} 1 & E = \text{sole off ground} \\ 0 & E = \text{heel striking ground} \end{cases}$$

$$ES_2 = \begin{cases} 1 & E = \text{heel off ground} \\ 0 & \text{timing } n \text{ seconds} \end{cases}$$

where $ES_1$ and $ES_2$ are the suprathreshold electrical stimulation performed on the tibialis anterior muscle and the gastrocnemius muscle respectively, E is the gait event identified in real time, 1 refers to performing the suprathreshold electrical stimulation, and 0 refers to stopping suprathreshold electrical stimulation.

12. The foot rehabilitation system of claim 1, wherein the suprathreshold electrical stimulation is a symmetrical square wave electrical stimulation with an amplitude of 70V, a frequency of 40 Hz, and a bandwidth of 50 us.

13. The foot rehabilitation system of claim 1, wherein the pneumatic musculoskeletal complex module (200) further comprises an electric air pump (106), an electric air valve (107) and an air pressure sensor (108).

14. The foot rehabilitation system of claim 13, wherein the pneumatic musculoskeletal complex module (200) is further configured to determine inflation or deflation of the pneumatic muscle (305) based on comparison of a value of air pressure in the pneumatic muscle (305) measured by the air pressure sensor (108) with a preset pressure threshold.

15. The foot rehabilitation system of claim 1, wherein the musculoskeletal complex (105) further comprises an exo-skeleton (301), and the exoskeleton (301) can be used as a container for all electronic devices, control circuit boards and batteries.

16. The foot rehabilitation system of claim 15, wherein the exoskeleton (301) is 3D printed from polylactide mate-rial.

17. The foot rehabilitation system of claim 15, wherein the exoskeleton (301) is connected to the pneumatic muscles (305) through an exoskeleton extension (303).

18. The foot rehabilitation system of claim 1, wherein the vibratory biofeedback module (109) comprises a vibration motor (402) located between a first toe and a second toe of the foot sole.

19. The foot rehabilitation system of claim 18, wherein the vibration motor (402) is controlled as follows:

$$Z = \begin{cases} 1, & FSR_{1\,max} \le FSR_{5max} \times b\ \% \\ 0, & FSR_{1\,max} > FSR_{5max} \times b\ \%, \text{ or } E = \text{heel striking ground} \end{cases}$$

where Z represents control of the vibration motor (402), Z=1 represents turning on the vibration motor (402), Z=0 represents stopping the vibration motor (402), $FSR_{1max}$ and $FSR_{5max}$ are respectively maximum values of the first pressure sensor at the first metatarsal head and the second pressure sensor at the fifth metatarsal head during a timing period after the heel is off the ground, b % is a preset balance threshold, and E is the gait event identified in real time.

20. The foot rehabilitation system of claim 1, wherein the rehabilitation system further comprises a fastening integration module (102) for securing the rehabilitation system to the foot.

21. The foot rehabilitation system of claim 15, wherein the fastening integration module (102) comprises a connector (304) for connecting and fixing the exoskeleton (301) and a position fixture (302) for fixing and cushioning a position of the pneumatic muscle (305).

22. The foot rehabilitation system of claim 20, wherein the fastening integration module (102) is made of breathable and elastic textile material.

23. The foot rehabilitation system of claim 1, wherein the pneumatic muscle (305) is a polyvinyl chloride film.

24. A use method of the gait event-driven, phase-dependent and multi-modal foot rehabilitation system of claim 1.

* * * * *